US011510626B2

(12) United States Patent
Schibli et al.

(10) Patent No.: US 11,510,626 B2
(45) Date of Patent: Nov. 29, 2022

(54) CONDUCTIVE POLYMER COMPOSITE BASED SENSOR

(71) Applicant: Heraeus Deutschland GmbH & Co. KG, Hanau (DE)

(72) Inventors: Stefan Schibli, Frankfurt am Main (DE); Heiko Specht, Hanau (DE); Ilias Nikolaidis, Frankfurt am Main (DE); Parth Bhimani, Bremen (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 923 days.

(21) Appl. No.: 15/972,351

(22) Filed: May 7, 2018

(65) Prior Publication Data

US 2018/0317849 A1 Nov. 8, 2018

(30) Foreign Application Priority Data

May 8, 2017 (EP) .................................. 17169888

(51) Int. Cl.
*A61B 18/14* (2006.01)
*A61B 5/00* (2006.01)
(Continued)

(52) U.S. Cl.
CPC .......... *A61B 5/6852* (2013.01); *A61B 5/6885* (2013.01); *A61B 18/1492* (2013.01);
(Continued)

(58) Field of Classification Search
CPC .......... A61B 2562/0261; A61B 5/6852; A61B 5/6885; A61B 18/1492; A61B 2090/065;
(Continued)

(56) References Cited

U.S. PATENT DOCUMENTS

2008/0161786 A1 7/2008 Belhe et al.
2010/0069733 A1* 3/2010 Kastelein ............. A61B 5/6857
600/374
(Continued)

FOREIGN PATENT DOCUMENTS

WO WO-2015189030 A1 * 12/2015 ............. B01J 23/38
WO 2017037117 3/2017

OTHER PUBLICATIONS

Yoshimura, Keijiro et al., "Flexible Tactile Sensor Materials Based on Carbon Microcoil/Silicone-Rubber Porous Composites," Computer Science and Technology, vol. 123, pp. 241-249 (2016).

*Primary Examiner* — Joanne M Hoffman
*Assistant Examiner* — Sean W Collins
(74) *Attorney, Agent, or Firm* — Dicke, Billig & Czaja, PLLC

(57) ABSTRACT

One aspect relates to a conductive polymer composite based sensor, a detection unit comprising such sensor, a method for manufacturing a conductive polymer composite based sensor, and a use of the conductive polymer composite based sensor or the detection unit. The conductive polymer composite based sensor includes a substrate and a sensor material. The sensor material includes an insulating polymer matrix component and an electrically conductive component dispersed in the polymer matrix component to form the conductive polymer composite. The sensor material is prestrained and applied to the substrate to form the sensor.

13 Claims, 3 Drawing Sheets

(51) Int. Cl.
   *A61M 25/00* (2006.01)
   *A61L 29/06* (2006.01)
   *A61L 29/02* (2006.01)
   *A61L 29/14* (2006.01)
   *G01L 1/18* (2006.01)
   *A61B 18/00* (2006.01)
   *A61B 90/00* (2016.01)

(52) U.S. Cl.
   CPC ............... *A61L 29/02* (2013.01); *A61L 29/06* (2013.01); *A61L 29/14* (2013.01); *A61L 29/146* (2013.01); *A61M 25/0009* (2013.01); *A61M 25/0045* (2013.01); *G01L 1/18* (2013.01); *A61B 2018/00577* (2013.01); *A61B 2090/065* (2016.02); *A61B 2562/0219* (2013.01); *A61B 2562/0247* (2013.01); *A61B 2562/0261* (2013.01); *A61B 2562/12* (2013.01); *A61B 2562/166* (2013.01)

(58) Field of Classification Search
   CPC .... A61B 2562/0219; A61B 2562/0247; A61B 5/268; A61B 5/263; A61B 5/25; G01L 1/18; A61M 25/0045; A61L 29/06; A61L 29/146; C01B 32/158
   See application file for complete search history.

(56) References Cited

U.S. PATENT DOCUMENTS

| | | | |
|---|---|---|---|
| 2011/0098549 A1* | 4/2011 | Bar Hayim | A61B 5/6833 600/391 |
| 2012/0259194 A1 | 10/2012 | Selkee | |
| 2012/0266685 A1* | 10/2012 | Choi | C08K 7/00 73/774 |
| 2014/0118884 A1* | 5/2014 | Lin | H01G 11/26 361/502 |
| 2017/0089782 A1* | 3/2017 | Hirt | A61B 5/6823 |
| 2017/0141405 A1* | 5/2017 | Neumann | C01B 32/20 |
| 2017/0203096 A1* | 7/2017 | Schibli | A61B 5/6846 |
| 2018/0242851 A1* | 8/2018 | Van Den Ende | H01L 41/042 |

* cited by examiner

CONDUCTIVE POLYMER COMPOSITE BASED SENSOR

CROSS-REFERENCE TO RELATED APPLICATION

This Utility patent application claims priority to Patent Application No. EP 17169888.9, filed on May 8, 2017, which is incorporated herein by reference.

BACKGROUND

One aspect relates to a conductive polymer composite based sensor, a detection unit comprising such sensor, a method for manufacturing a conductive polymer composite based sensor, and a use of the conductive polymer composite based sensor or the detection unit. The conductive polymer composite based sensor may be used in an electrophysiology ablation catheter.

Heart disease is the leading cause of death in the world, which includes heart stroke and other cardiovascular diseases. Among all another heart diseases, cardiovascular disease is the leading global cause of death. Arrhythmia is a class of heart diseases, which defines as certain change from normal heart rhythm. During arrhythmia, the heart beats too fast or too slow. In other words, the heartbeat has become irregular.

A person with any kind of arrhythmia has to go through a surgical procedure called catheter ablation. During this surgical procedure, a catheter is inserted in the heart through blood vessels. It has a tip sensor, which measures the force between body tissue and a catheter tip. This force is monitored by the physician during the surgery to protect the heart wall. To cure the arrhythmia, damaged tissue is destroyed by a process called ablation.

An object in catheter ablation is to maintain a contact force between the catheter tip and tissue for sensing and energy delivery for ablation. If the force is not sufficiently controlled and monitored, there can be collateral damages in areas where ablation is not required.

As a result, there may be a need to provide an improved conductive polymer composite based sensor, which allows an improved sensitivity. For these and other reasons, a need exists for the present embodiments.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
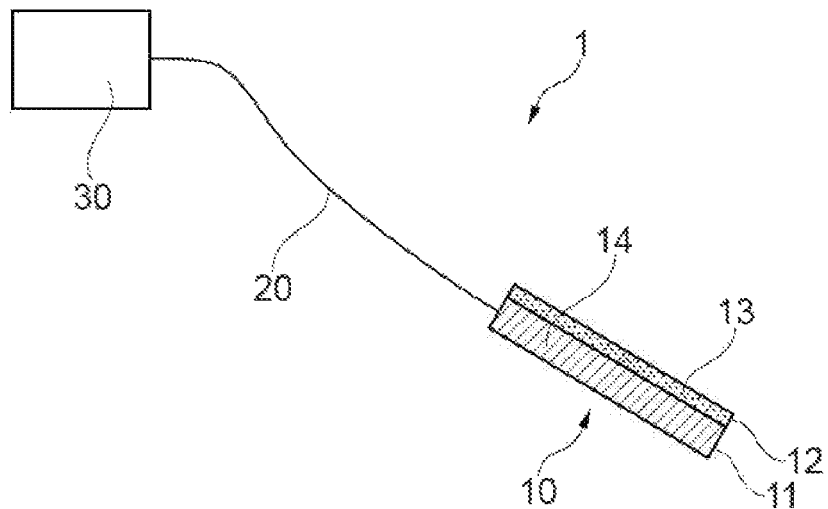
FIG. 1 illustrates schematically and exemplarily an embodiment of a detection unit according to one embodiment.

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

Certain aspects are solved by the subject-matters of the independent claims; wherein further embodiments are incorporated in the dependent claims. It should be noted that the aspects of the invention described in the following apply also to the conductive polymer composite based sensor, the detection unit comprising such sensor, the method for manufacturing a conductive polymer composite based sensor and the described use of the conductive polymer composite based sensor or the detection unit.

According to one embodiment, a conductive polymer composite based sensor is presented. The sensor includes a substrate and a sensor material. The sensor material includes an insulating polymer matrix component and an electrically conductive component dispersed in the polymer matrix component to form the conductive polymer composite. The sensor material is pre-strained and applied to the substrate to form the sensor.

As a result, one embodiment refers to a conductive polymer composite based sensor with at least one of the following advantages: a possibility to form sensors illustrating superior sensitivity, a possibility to form very small sensors, a possibility to form flexible sensors, and a possibility to form a sensors with a large measuring or detection range, a small dependence on temperatures and/or a very good relaxation behavior. Further, the conductive polymer composite based sensor according to one embodiment may allow an easy and cheap manufacture, may be manufactured in all kinds of shapes and sizes and may be adapted during manufacture in view of its elastic modulus, flexibility etc. by for example, tuning the physical properties of the insulating polymer matrix component.

In an example, the sensor is configured to measure force, pressure, strain, movement, acceleration, vibration and/or changes thereof. In an example, the substrate is a medical device, for example, catheter and further for example, an electrophysiology ablation catheter.

The pre-straining may be an elongation in the range of 1 to 50% of the initial length, in one embodiment in the range of 5 to 20%, and in one embodiment in the range of 7 to 15%. Elongation is here calculated as a change of length Δl divided by an initial length l0, for example 3 mm/12 mm=0.25, and the result multiplied by 100 to give the amount as percentage, here for example, 25%.

In an example, the electrical resistance is decreasing constantly and consistently with increased elongation and it is increased when the sensor material is allowed to go back to its initial length. The pre-straining may allow modifying the behavior of the material so that the resistance is always decreasing with additional stress applied and is always increasing with stress relieved. If the sensor is not pre-strained, then upon applying the very first stress the resistance would increase, flowing a certain stress (which has been found to be less than 8%) this behavior would be reversed and the resistance would start decreasing with stress. The same effect would take place when removing stress from the sensor. This is the reason why pre-straining is considered beneficial and necessary.

In an example, the insulating polymer matrix component is an elastomer and for example, a silicone elastomer. In an example, the electrically conductive component is a carbon component, which for example, includes porous carbon particles.

When a load, as for example, mechanical pressure, is applied to the conductive polymer composite based sensor, polymeric chains of the polymer matrix component may be compressed and particles of the electrically conductive component may contact each other to implement or improve an electric conductivity. The polymeric chains may infiltrate or penetrate through pores within particles of the electrically conductive component and may also extend between the particles of the electrically conductive component and thereby link several carbon particles to each other. This means, when mechanical stress is applied to the compound of polymer matrix component and conductive component, the compound illustrates a change of its electrical resistivity and for example, a decrease of its electrical resistivity and an increase of electrical conductivity (piezoresistive effect).

In an example, the electrically conductive component is a carbon component. In an example, the carbon component includes porous carbon particles. An advantage in one embodiment may be that porous carbon particles are more mechanically linked due to a polymer penetration of the pores in the porous carbon particles. This results in a reduced risk of particle migration, and therefore, less creep in electrical response. The porous carbon particles can be Heraeus Porocarb.

The term "carbon component" may be understood as a component comprising carbon particles with open porosity and macropores.

The term "porous" may be understood as having a total pore volume between 0.7 and 3.5 cm$^3$/g, and in one embodiment between 0.9 and 2.5 cm$^3$/g.

In an example, the carbon particles include macropores. The term "macropores" may be understood as pores having a size between 50 and 1000 nm measured by, for example Hg porosimetry. In an example, the macropores in the carbon particles have a macropore volume between 0.6 and 2.4 cm$^3$/g, and in one embodiment between 0.8 and 2.2 cm$^3$/g. The dimensions of the macropores of the carbon particles may be adapted to the dimensions of polymeric precursors of the polymer matrix component. This means, the diameter of a polymer emulsion particle is in a range of a diameter of a macropore. The interconnection between carbon particles and polymer matrix component may also include that at least some of the carbon particles are linked by polymeric chains. Such rigid mechanical interconnection between carbon particles and polymeric chains enables a most complete geometrical restoring after elastic compression of the material.

In an example, the carbon particles further include mesopores. The term "mesopores" may be understood as pores having a size between 2 and 50 nm measured by, for example Hg porosimetry. In an example, the mesopores in the carbon particles have a mesopore volume between 0.05 and 0.2 cm$^3$/g, and in one embodiment between 0.1 and 0.15 cm$^3$/g.

In an example, the carbon particles include essentially no micropores. The term "micropores" may be understood as pores having a size smaller than 2 nm measured by nitrogen adsorption (BET). In an example, the micropores in the carbon particles have a micropore volume of less than 0.01 cm$^3$/g.

In an example, the electrically conductive component is graphitized. The term "graphitized" may be understood in that a formation of graphitic carbon is initiated by an exposure to elevated temperatures between, for example 1400 to 3000° C. During graphitization, micropores tend to disappear, mesopores rearrange and macropores remain constant. The result may be a graphitized, porous carbon component comprising carbon particles with a large amount of macropores. The macropores can be linked or interconnected with each other. The formation of graphite in the carbon component leads to an increased electrical conductivity. The graphitizing of the carbon component may here be done between 1400 and 3000° C., in one embodiment between 2300 and 2600° C.

In an example, the electrically conductive component is graphitized to a graphitization degree between 60 and 80%, and in one embodiment to a graphitization degree of over 70%. The graphitization degree g may be calculated based on a measured distance d002 of graphite basal levels: g=(344 pm−d002)/(344 pm−335.4 pm) A small distance d002 value thereby relates to a high graphitization degree. In an example, the carbon particles have sizes d50 between 1 and 100 μm, in one embodiment between 5 and 20 μm.

In an example, the electrically conductive component has a real density between 1.6 and 2.26 g/cm$^3$, and in one embodiment between 2.0 and 2.26 g/cm$^3$ as measured by He pycnometry.

In an example, the electrically conductive component has a specific surface between 5 and 500 m2/g, and in one embodiment between 10 and 70 m2/g. The specific surface is here measured according to BET (Brunauer-Emmett-Teller).

In an example, the amount of the electrically conductive component in the insulating polymer matrix component is between 1 to 30 wt.-%, in one embodiment between 15 and 26 wt.-%. In an example, only pores of the electrically conductive component, which are larger than a filling threshold, are infiltrated by polymeric chains of the polymer matrix component. Exemplarily, the filling threshold is between 60 and 250 nm, and in one embodiment between 60 and 150 nm.

In an example, the insulating polymer matrix component includes rubber and/or silicone. Rubber may be styrene butadiene rubber, ethylene propylene diene monomer rubber or the like. Silicone may have a viscosity in an uncured state between 10 Pa s and 2000 Pa s when measured, for example according to DIN53019.

According to one embodiment, also a detection unit is presented. The detection unit includes a conductive polymer composite based sensor as described above, a conductor and a processing element.

The conductor is configured for transferring a signal from the conductive polymer composite to the processing element. The processing element is configured to process a signal provided by the conductive polymer composite based sensor.

The detection element may be part of an electrophysiology ablation catheter or another catheter tip.

In an example, the conductive polymer composite based sensor is a piezoresistive sensor. The term "piezoresistive" may be understood in that the piezoresistive sensor is subjected to a change of its electrical resistivity when mechanical stress is applied to the piezoresistive sensor. The mechanical stress may be an elastic, isostatic or unidirectional compressive load. The mechanical stress may be at least one of a group comprising force, pressure, motion, vibration, acceleration and elongation.

In an example, the processing element is configured to process a change of electrical resistance detected by the sensor into a mechanical load applied to the sensor. The processing element may be an analog digital converter.

According to one embodiment, also a method for manufacturing a conductive polymer composite based sensor is presented. It includes the following steps:

a) providing a sensor material comprising an insulating polymer matrix component and an electrically conductive component dispersed in the polymer matrix component to form the conductive polymer composite, b) pre-straining the sensor material, and c) applying the sensor material to a substrate to form the sensor.

In an example, the providing of the sensor material includes a pressing of uncured sensor material through a cylindrical die to form at least one sensor material rod. Exemplarily, the die may have several holes with about 239 μm diameter to form several extruded material rods of about 320 μm diameter by pressing a piston into the die. The extrusion may be done manually and for example at a speed in the range of 0.5 to 3 cm per second, and more in one embodiment at a speed in the range of 0.9 to 1.5 cm per second.

In an example, the providing of the sensor material further includes a cutting of the sensor material rod to an initial sensor length. The initial sensor length may be about 20 mm.

In an example, the providing of the sensor material further includes a curing of the sensor material in one embodiment between 150 and 250° C. for between 1 and 2 hours.

In an example, one end of the sensor material is taped to the substrate by means of an adhesive tape; the other end is pre-strained and then also taped to the substrate. In another example, the sensor material is first pre-strained and then the ends of the sensor material are taped to the substrate.

In an example, the pre-straining of the sensor material includes a pulling of the sensor material to an elongated sensor length. In an example, the pre-straining of the sensor material includes a pulling to an elongation between 1 to 50%. The elongation may also be between 5 to 20% and in one embodiment between 7 to 15%.

In another example, the pre-straining of the sensor material includes a compression of the sensor material.

In an example, the application of the sensor material to the substrate includes a gluing of the sensor material on at least one pair of electrodes of the substrate by means of an electrically conductive adhesive.

In an example, the application of the sensor material to the substrate further includes a curing of the adhesive in one embodiment between 100 and 200° C. for between 5 and 15 minutes.

In an example, the method for manufacturing the conductive polymer composite based sensor further includes a cutting of the sensor material extending over the electrodes or the corresponding glue spots. This cutting step may also include a removal of the adhesive tape and of all temporary features extending over the electrodes.

In an example, the method further includes a step of graphitizing the carbon component between 1400 and 3000° C., in one embodiment between 2300 and 2600° C.

According to one embodiment, also a use of the conductive polymer composite based sensor or the detection unit as described above for an electrophysiology ablation catheter is presented. Such ablation catheter allows a better control of ablation parameters.

In an example, the conductive polymer composite based sensor or the detection unit as described above is used for a probe to detect a force, pressure, motion and/or vibration of the probe relative to a surrounding medium. Further, a detection of a change in force, pressure, motion, vibration etc. is possible. In addition, a detection of acceleration or elongation or their changes is possible. The surrounding medium may be gaseous, liquid or solid. It may be bone, tissue, organs, blood and/or the like. When using several probes, also a detection of a position of an occurrence or a change in force, pressure, motion, vibration etc. is possible.

It shall be understood that the conductive polymer composite based sensor, the detection unit comprising such sensor, the method for manufacturing a conductive polymer composite based sensor and the described use of the conductive polymer composite based sensor or the detection unit according to the independent claims have similar and/or identical embodiments, for example, as defined in the dependent claims. It shall be understood further that embodiments can also be any combination of the dependent claims with the respective independent claim.

Catheter ablation is a surgical procedure for cardiac arrhythmia, which uses radiofrequency energy to destroy heart tissue that causes rapid and irregular heartbeat. Destroying these heart tissue helps to restore the normal heartbeat rhythm.

Catheter ablation is generally performed by a Cardiac Electrophysiologist, a person who is specialized in diagnosing and treating arrhythmia disorder. During the catheter ablation, a specially designed flexible wire called catheter is inserted into a blood vessel under X-ray guidance and guided through veins until it reaches to heart.

The present contact force sensing catheter technology allows an accurate measurement of the exact contact force between tissue and catheter tip.

FIG. 1 illustrates schematically and exemplarily an embodiment of a detection unit 1 according to one embodiment. The detection unit 1 includes a conductive polymer composite based sensor 10, a conductor 20 and a processing element 30. The detection unit 1 may be part of an electrophysiology ablation catheter.

The conductor 20 is configured for transferring a signal from the conductive polymer composite to the processing element 30.

The processing element 30 is configured to process a signal provided by the conductive polymer composite based sensor 10.

The conductive polymer composite based sensor 10 includes a substrate 11 and a sensor material 12. The sensor material 12 includes an insulating polymer matrix component 13 and an electrically conductive component 14 dispersed in the polymer matrix component 13 to form the conductive polymer composite. The sensor material 12 is pre-strained and applied to the substrate 11 to form the sensor 10. The conductive polymer composite based sensor 10 is a piezoresistive sensor. This means that polymeric chains of the insulating polymer matrix component 13 rearrange and relax between carbon particles of the electrically conductive component 14 when the sensor material 12 is subjected to a compressive load by, for example bending. The rearrangement and relaxation enables a formation of electrical paths between the electrically conductive carbon particles and consequently reduces the electrical resistance of the piezoresistive sensor material 12.

Figure 2:
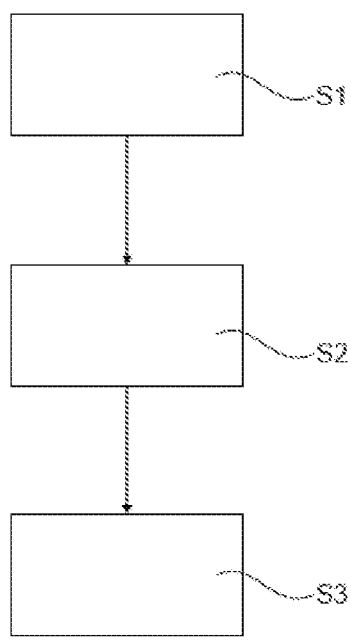
FIG. 2 illustrates a schematic overview of a method for manufacturing a conductive polymer composite based sensor according to one embodiment.

FIG. 2 illustrates a schematic overview of steps of a method for manufacturing a conductive polymer composite based sensor 10 according to one embodiment. The method includes the following steps:

In a first step S1, providing a sensor material 12 comprising an insulating polymer matrix component 13 and an electrically conductive component 14 dispersed in the polymer matrix component 13 to form the conductive polymer composite.

In a second step S2, pre-straining the sensor material 12.

In a third step S3, applying the sensor material 12 to a substrate 11 to form the sensor 10.

A detailed embodiment of the method for manufacturing a conductive polymer composite based sensor 10 is explained in the following example:

To prepare a conductive polymer sample, two-component polymer matrix liquid phase silicone Elastosil® LR 3003/10 with a shore hardness of 10 from Wacker Chemie AG is used along with various conductive composites such as carbon nanotubes, carbon black, aluminum oxide and Heraeus Porocarb. Two component silicone contains a platinum catalyst and cross-linkers, which react immediately after mixing. Silicone works as a filler during a curing procedure of the conductive polymer. Fillers are required to reinforce the elastic silicone network, which makes the conductive polymer solid and elastic like rubber. Elastosil® LR 3003/10 has a high viscosity of $\eta=74,000$ mPa*s with a shear rate of 0.9 s-1. The high viscosity of the polymer matrix provides a high shear force during dispersion of the conductive composite in the polymer matrix, which according to one embodiment is advantageous during the production of the conductive polymer material. Distributing and separating fillers in the polymer matrix has major influence on the electrical properties of the conductive polymer. The dispersing of the conductive composite in the polymer matrix is achieved by using a three roll mill.

The three roll mill includes three cylindrical rollers, which can rotate at different speeds and distances. The first and last roller rotate in the same direction while the middle roller rotates in an opposite direction. When material is fed between the first two rollers, the material flows through the third roller because of the high viscosity of silicone.

In order to prepare a sample of sensitive material, the same weight percentage (wt %) of conductive composite such as carbon nanotubes, carbon black or Heraeus Porocarb is mixed with silicone A and silicone B.

After the dispersion of conductive composites in the polymer matrix using the three roll mill, both silicone A and B filled conductive composites are mixed in the ratio of 1:1. To produce the sensor material for the catheter tip, these mixed conductive composites are extruded using a hydraulic press machine and a cylindrical drawing die, which has an opening of 0.239 mm. After extruding the sensor material 12 in form of a rod by applying pressure through the drawing die, the material rod is cured in an industrial oven for 1.5 hours at 200° C. This curing process interlinks the silicone component with the conductive composite and turns it into a conductive polymer.

The sensor material 12 is connected to an electrode by dispensing a conductive adhesive (Heraeus conductive adhesive PC 3001) on both ends of the material and it is cured at 150° C. for 10 minutes. This conductive adhesive is a one-component, silver filled epoxy conductive adhesive and especially designed for connection of electronics (SMDs) and ceramic substrates. A suitable curing profile is selected. High electrical and thermal conductivity allows noise free sensor output data. The use of the conductive adhesive for the electrical connection of the sensor material 12 minimizes an effect of unwanted deflection and compression.

To investigate a piezoresistivity and suitability of the sensor material 12 for an EP ablation catheter, various measurement tests have been performed such as a static force test and a strain test. Heraeus Porocarb is selected as conductive polymer material. The input force is applied to a sensor using a Zwick Roell tensile machine and a resistance change of the sensor material 12 along with the applied input force is recorded using the digital multimeter Agilent 34401.

To investigate a repeatability and response of a sensor 10 towards step input, a step strain test has been performed. In the step strain test, the sensor material 12 is elongated by step strain input (elongation) such as 1 mm, 2 mm and 3 mm. The sensor 10 has been elongated between two step strain inputs for 120 seconds. This strain test proves the ability of sensor 10 to measure two discrete input signals. The behavior of the sensor 10 is beneficial in order to identify a change of applied force on tissue by during catheter ablation.

To demonstrate a contact force sensing of the catheter tip sensor, a polyurethane catheter with a diameter of 2 mm is designed. Since the conductive polymer is sensitive enough to measure the strain quantity, three sensors are embedded in the tip area of the catheter. This design of the catheter allows measuring a directional force when the catheter is bent.

Figure 3:
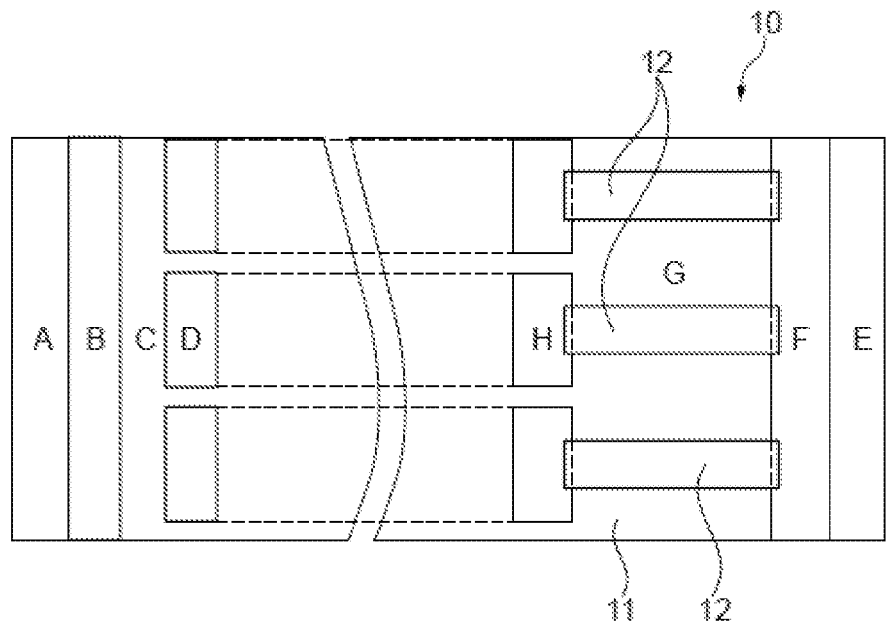
FIG. 3 illustrates a conductive polymer composite based sensor according to one embodiment.
Figure 4:
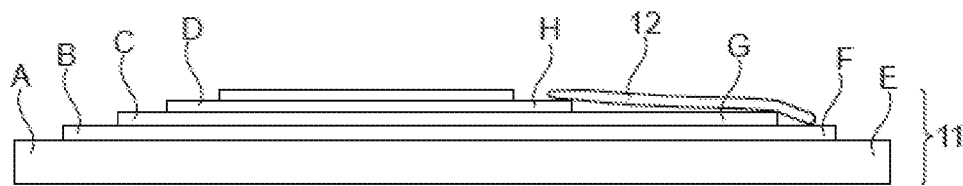
FIG. 4 illustrates a different perspective of the conductive polymer composite based sensor according to FIG. 3.

FIGS. 3 and 4 illustrate different perspectives of a conductive polymer composite based sensor 10 according to one embodiment. The catheter has a diameter of 2 mm, which is an average diameter for an ablation catheter. The hollow catheter includes as substrate 11 a polyurethane tubing A, E with a multi-level metallization circuit B, C, D, F, G, H. The multi-layer circuit is designed to embed three sensors made of the sensor material 12 on the tip area of catheter. The first layer B, F of the circuit is printed in the form of a continuous conductive layer and the second layer D, H of the circuit includes three distinct axial conductive pathways. These two conductive layer B, F and D, H as well as a middle section of the second layer D, H are electrically isolated by dielectric layer C, G and a top dielectric layer in order to avoid a short-circuit. These conductive paths are made of a silver conductive ink and cured by a UV curing process.

As illustrated in FIGS. 3 and 4, the first conductive layer B, F includes one common printed electrode and the second conductive layer D, H includes three printed electrodes, where three sensors made of the sensor material 12 will be embedded. All three sensors are at an interval of 120° angle in order to have a maximum sensitive catheter tip area, which provides a directional force sensing. The sensor output signal can be measured using electrodes B and D when the input force is applied to the catheter by bending the catheter. The three subparts of the second conductive layer D, H are inter-connected which is illustrated by a dotted line. These parts transfer an output signal of the sensor 10 when the sensor 10 experiences an elongation.

The catheter or the substrate 11 has three sensors made of the sensor material 12 on a top area. All sensor material rods are cut to an equal length. For a sensor rod, a pre-stretching condition is defined in order to have consistent output response. In order to pre-stretch the material rod, both ends of the material rod are fixed on the catheter using an adhesive tape. The adhesive tape helps to keep the material stretched. As soon as all material rods are fixed on the catheter by the adhesive tape, the conductive adhesive is applied on both sides of the material rod to connect the material to the printed electrode in order to form the sensor 10. On the opposite side of the catheter, an output signal of the sensor 10 will be measured. Electrical wires are attached to the respective printed electrodes. The whole assembly of the catheter tip sensor is treated at 150° C. for 10 minutes to cure the conductive adhesive. This curing process will harden the conductive adhesive, which is applied on material rod. The designed catheter will measure a contact force when a force is applied on the catheter tip, which has three sensors on the surface of the catheter.

Figure 5:
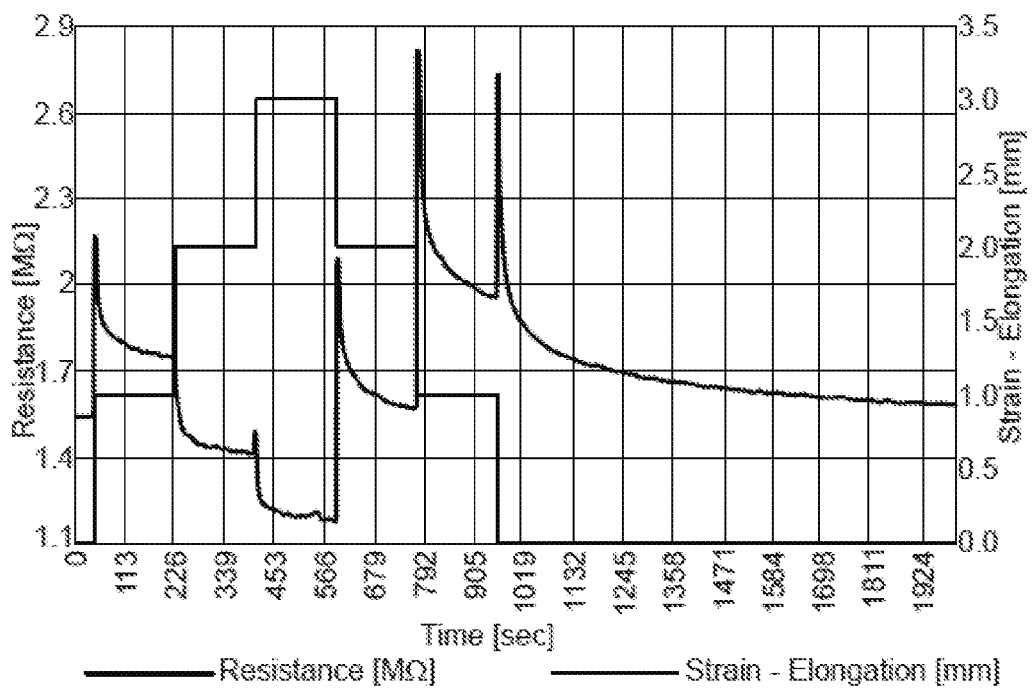
FIG. 5 illustrates the results of a step strain test without pre-strain.

FIG. 5 illustrates the results of a step strain test without pre-strain. During the step strain test, the sensor 10 is elongated at a rate of 10 mm/min which means it will take 6 seconds for 1 mm of elongation. The length of the material is kept the same (initial length of material=12 mm). During the step strain test, the sensor 10 is elongated by 3 mm with a strain step of 1 mm. A dwell time for this step strain test is 3 minutes to observe the creep behavior of the sensor 10.

When the sensor 10 is elongated by 1 mm, a resistance of the sensor 10 is increased by 29.8%. During the following two step elongation, the resistance dropped by 15.8% and 12.7%. When the elongation is released, with each step of elongation releasing resistance of material hikes by 71.6%, 78.3% and 39.3% respectively. In other words, in the very early stages of elongation, the resistance is increasing, followed by a decrease in resistance for further elongation. The same thing in the opposite direction is noticed when the material is relaxed. For the first couple of steps (relaxing from 3 mm down to 1 mm of elongation), the resistance is increasing with every such step. Nevertheless, for the very last step (relaxing from 1 mm elongation to 0 elongation), there is a decrease in resistance. As a result, the material does not give a consistent output response during the step strain test. It also illustrates a large amount of hysteresis and creep behavior during the elongation release stage.

Figure 6:
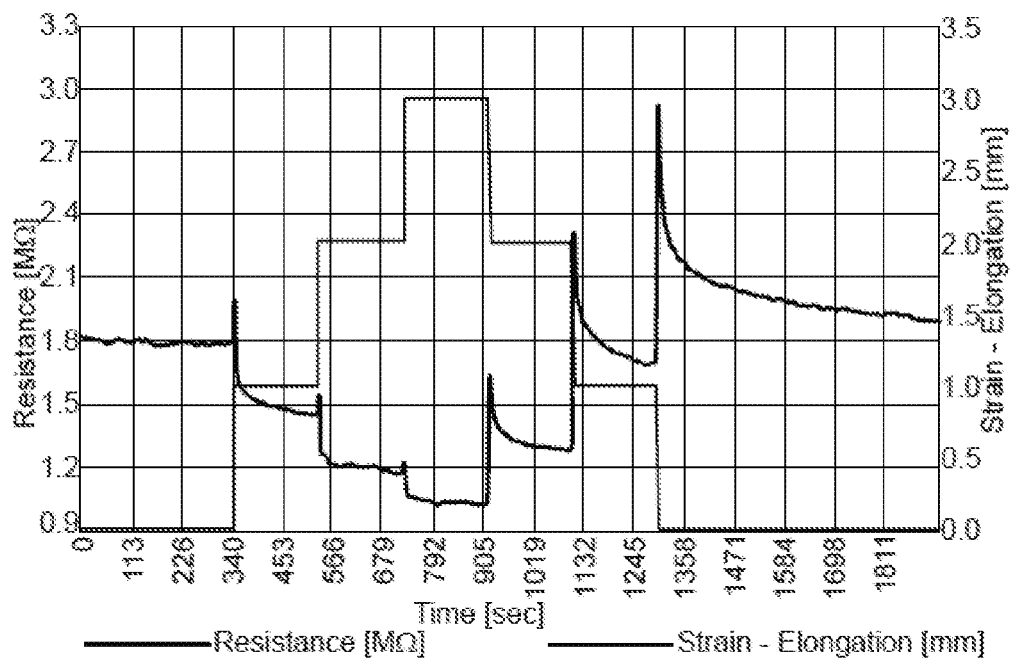
FIG. 6 illustrates the results of a step strain test with pre-strain.

FIG. 6 illustrates the results of a step strain test with pre-strain. During the pre-stretch step strain step, the material is pre-stretched by 1 mm (original length of material=12 mm, pre-stretched material length=13 mm). During the steps of elongation, the resistance of the material declines by 20%, 13% and 8.3% for the elongation of 1 mm, 2 mm and 3 mm, respectively. When the elongation is released, the resistance went up by 49.5%, 75% and 64.7% for the elongation release of 2 mm, 1 mm and 0 mm, respectively. In other words, resistance is constantly and consistently decreasing with increased elongation and it is increased when the material is allowed to go back to its original shape.

Therefore, in order to achieve a consistent behavior of this sensor 10, which means a consistent output response (resistance change in the same direction when the strain is applied), pre-stretching of the material is necessary.

It has to be noted that embodiments are described with reference to different subject matters. For example, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While embodiments have been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

What is claimed is:

1. A conductive polymer composite based sensor, comprising:
   a substrate, and
   a sensor material,
   wherein the sensor material comprises an insulating polymer matrix component and an electrically conductive component dispersed in the polymer matrix component to form the conductive polymer composite;
   wherein the electrically conductive component is a carbon component,
   wherein the sensor material is pre-strained,
   wherein the sensor material is applied to the substrate to form the sensor;
   wherein the carbon component comprises porous carbon particles and the porous carbon particles have sizes d50 between 1 and 100 µm; and
   wherein the sensor material has an initial length and a final length, and the sensor material is pre-strained by an elongation to the final length in a range of 1 to 50% of the initial length.

2. The sensor of claim 1, wherein the substrate is a catheter.

3. The sensor of claim 1, wherein the insulating polymer matrix component is a silicone elastomer.

4. The sensor of claim 1, wherein the porous carbon particles have a total pore volume between 0.7 and 3.5 $cm^3/g$.

5. The sensor of claim 1, wherein the porous carbon particles comprise macropores and wherein the macropores have a size between 50 and 1000 nm.

6. The sensor of claim 1, wherein the macropores in the porous carbon particles have a macropore volume between 0.6 and 2.4 cm$^3$/g.

7. The sensor of claim 1, wherein the porous carbon particles further comprise mesopores with a size between 10 and 50 nm and a mesopore volume between 0.05 and 0.2 cm$^3$/g.

8. The sensor of claim 1, wherein the porous carbon particles comprise essentially no micropores with a size smaller than 2 nm.

9. The sensor of claim 4, wherein the carbon component is graphitized to a graphitization degree between 60 and 80%.

10. The sensor of claim 1, wherein the sensor is configured to measure force, pressure, strain, movement, acceleration, vibration and/or changes thereof.

11. The sensor of claim 1, wherein the sensor is configured as an electrophysiology ablation catheter.

12. A detection unit, comprising:
a conductive polymer composite based sensor according to claim 1;
a conductor; and
a processing element;
wherein the conductor is configured for transferring a signal from the conductive polymer composite to the processing element, and
wherein the processing element is configured to process the signal provided by the conductive polymer composite based sensor.

13. The detection unit of claim 12, wherein the conductive polymer composite based sensor is a piezoresistive sensor and the processing element is configured to process a change of electrical resistance detected by the conductive polymer composite based sensor into a mechanical load applied to the conductive polymer composite based sensor.

* * * * *